United States Patent
Lachenbruch

(10) Patent No.: US 9,222,685 B2
(45) Date of Patent: Dec. 29, 2015

(54) METHOD AND SYSTEM FOR CONTROLLING EVAPORATIVE AND HEAT WITHDRAWAL PERFORMANCE OF AN OCCUPANT SUPPORT SURFACE

(75) Inventor: Charles A Lachenbruch, Lakeway, TX (US)

(73) Assignee: Hill-Rom Services, Inc., Batesville, IN (US)

(*) Notice: Subject to any disclaimer, the term of this patent is extended or adjusted under 35 U.S.C. 154(b) by 945 days.

(21) Appl. No.: 12/836,606

(22) Filed: Jul. 15, 2010

(65) Prior Publication Data

US 2012/0012277 A1    Jan. 19, 2012

(51) Int. Cl.
| | |
|---|---|
| *F24F 3/044* | (2006.01) |
| *A47C 21/04* | (2006.01) |
| *A61F 7/00* | (2006.01) |
| *F24F 3/14* | (2006.01) |
| *F24F 5/00* | (2006.01) |

(52) U.S. Cl.
CPC ............... *F24F 3/044* (2013.01); *A47C 21/044* (2013.01); *A61F 7/00* (2013.01); *F24F 3/14* (2013.01); *F24F 5/0096* (2013.01); *A61F 2007/0057* (2013.01); *A61G 2210/70* (2013.01); *A61G 2210/90* (2013.01)

(58) Field of Classification Search
CPC ........ A47C 21/044; A47C 21/00; A61F 7/00; A61F 2007/0057; A61G 2210/90; A61G 2210/70; F24F 3/044; F24F 3/14; F24F 5/0096; F24F 7/00
USPC .......... 62/121, 171, 176.1, 176.6, 259.4, 261; 165/46, 222, 229, 230; 5/421, 423
See application file for complete search history.

(56) References Cited

U.S. PATENT DOCUMENTS

| | | | | |
|---|---|---|---|---|
| 2,093,834 | A * | 9/1937 | Gaugler | 4/536 |
| 3,736,764 | A * | 6/1973 | Chambers et al. | 62/89 |
| 3,757,366 | A * | 9/1973 | Sacher | 5/423 |
| 4,543,637 | A * | 9/1985 | Smith et al. | 700/269 |
| 5,016,304 | A * | 5/1991 | Ryhiner | 5/689 |
| 5,921,314 | A * | 7/1999 | Schuller et al. | 165/43 |
| 6,855,158 | B2 * | 2/2005 | Stolpmann | 607/108 |
| 7,469,572 | B2 * | 12/2008 | Bartlett | 73/29.01 |
| 7,975,331 | B2 * | 7/2011 | Flocard et al. | 5/423 |
| 2008/0263776 | A1 * | 10/2008 | O'Reagan et al. | 5/714 |
| 2009/0064411 | A1 * | 3/2009 | Marquette et al. | 5/423 |

* cited by examiner

Primary Examiner — Frantz Jules
Assistant Examiner — Joseph Trpisovsky
(74) Attorney, Agent, or Firm — Barnes & Thornburg LLP

(57) ABSTRACT

A method for controlling performance of an MCM capable support surface having a flowpath for guiding a stream of air along at least a portion of the surface, comprises specifying a desired evaporative rate greater than an evaporative rate achievable with unconditioned ambient air, chilling the unconditioned ambient air to a temperature at least as low as that required to achieve 100% relative humidity, thereby demoisturizing the air, and supplying the chilled, demoisturized air to the flowpath. The method may also include the step of heating the chilled, demoisturized air prior to step of supplying it to the flowpath. A system for carrying out the method includes a microclimate management (MCM) capable support surface 22, a chiller 60 for cooling air to be delivered to the MCM capable surface, a user interface 42 for receiving instructions concerning desired microclimate management performance, and a controller 50, responsive to the instructions, for operating the chiller.

20 Claims, 8 Drawing Sheets

METHOD AND SYSTEM FOR CONTROLLING EVAPORATIVE AND HEAT WITHDRAWAL PERFORMANCE OF AN OCCUPANT SUPPORT SURFACE

TECHNICAL FIELD

The subject matter described herein relates to occupant support surfaces, such as hospital bed mattresses having microclimate management capabilities, and to methods and systems for controlling the evaporative performance and heat withdrawal performance of the support surface.

BACKGROUND

Hospital beds may be equipped with a support surface having microclimate management (MCM) capability. MCM capability refers to the capability to affect the environment, particularly the temperature and humidity, in the immediate vicinity of the bed occupant. The MCM-capable support surface may be a topper installed on a mattress, or may be the mattress itself. Effective microclimate management can benefit a bed occupant by resisting or mitigating the effects of skin tissue breakdown.

A typical MCM-capable support surface has provisions for receiving and discharging a stream of air. At least that portion of the support surface upon which the occupant rests is vapor permeable. In operation, a stream of air flows through the interior of the support surface. Provided the air is cooler than the occupant's skin, the internal airstream acts as a heat sink to keep the occupant's skin cool, thereby reducing the metabolic demands of the skin tissue and, as a consequence, reducing the likelihood that the occupant will develop pressure ulcers. This mode of heat transfer is proportional to the temperature gradient between the occupant's skin and the airstream ($dq_{DRY}/dt = k_1 \Delta T$) and is referred to herein as "dry flux", DF.

In addition, heat transfer from the occupant's skin can cause molecules of perspiration present at the interface between the support surface and the occupant's skin to acquire enough energy to break free, i.e. evaporate, from the liquid perspiration. The liberated molecules migrate through the vapor permeable portion of the occupant support, and are carried away in the internal airstream. The attendant moisture reduction at the skin/surface interface is beneficial because dry skin is less vulnerable to tissue breakdown than wet skin provided the skin is not excessively dry. Moreover, because the evaporation is the result of heat transfer from the occupant, the occupant experiences an evaporative cooling effect above and beyond the above described dry flux. This evaporative mode of heat transfer is proportional to the difference between $P_{H2O,SKIN}$, the partial pressure of water vapor (perspiration) at the occupant's skin (i.e. at the occupant/surface interface) and $P_{H2O,STREAM}$, the partial pressure of water vapor in the airstream ($dq_{WET}/dt = k_2 \Delta P_{H2O}$) and is referred to herein as "wet flux", WF. The wet flux component of heat transfer materializes only when the occupant is perspiring and depositing liquid phase perspiration at the skin/surface interface.

Typically, the air flowing through the MCM-capable surface is ambient air (e.g. air from a hospital room), unconditioned in the sense that no temperature and/or humidity conditioning has been applied to the air above and beyond the conditioning applied by the hospital heating, ventilating and air conditioning (HVAC) system. As a result, the effectiveness of the MCM-capable support surface is constrained by the properties of the room air. What is needed is a way to selectively achieve enhanced microclimate performance and to govern the degree of enhancement.

SUMMARY

A method for controlling performance of an MCM capable support surface having a flowpath for guiding a stream of air along at least a portion of the surface, comprises specifying a desired evaporative performance greater than an evaporative performance achievable with unconditioned ambient air, chilling the unconditioned ambient air to a temperature at least as low as that required to achieve 100% relative humidity, thereby demoisturizing the air, and supplying the chilled, demoisturized air to the flowpath. The method may also include the step of heating the chilled, demoisturized air prior to the step of supplying it to the flowpath.

BRIEF DESCRIPTION OF THE DRAWINGS

The foregoing and other features of the various embodiments of the system and method for enhancing and controlling microclimate performance of a support surface described herein will become more apparent from the following detailed description and the accompanying drawings in which.

DETAILED DESCRIPTION

Figure 1:
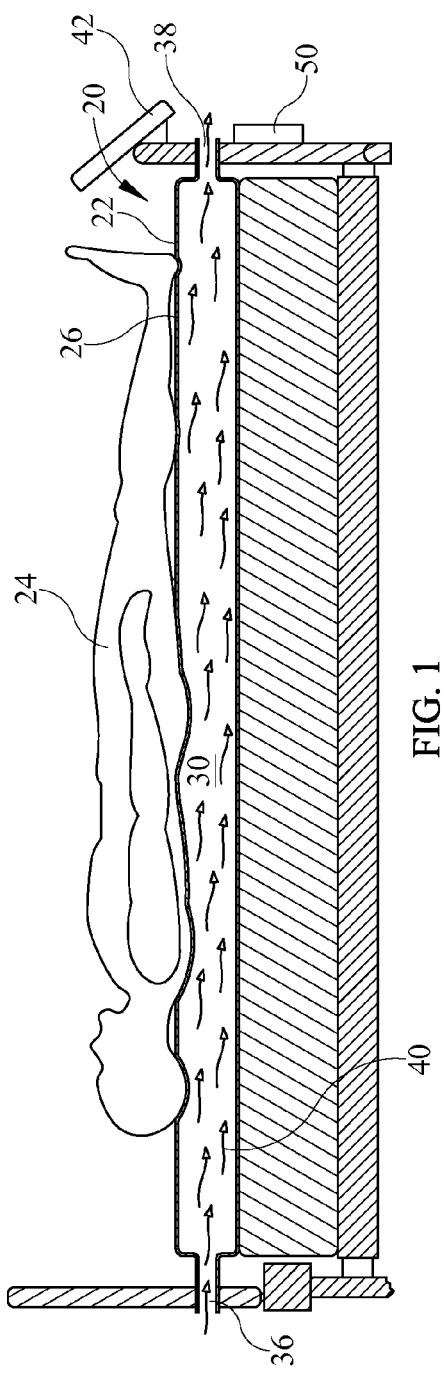
FIG. 1 is a schematic, side elevation view of a bed having an MCM-capable support surface.
Figure 2:
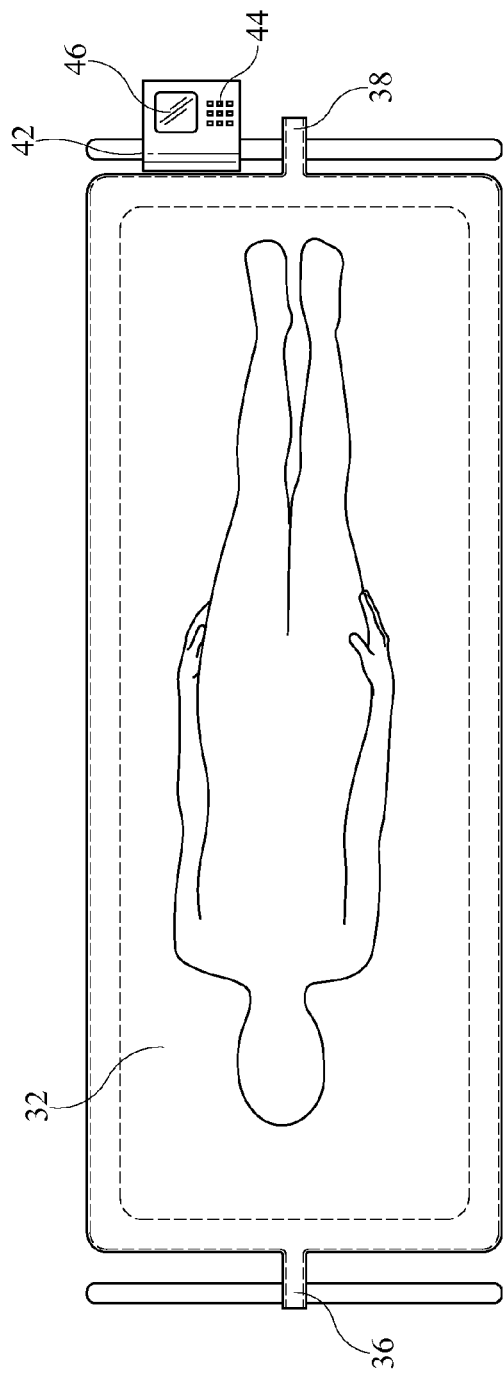
FIG. 2 is a view taken in the direction 2-2 of FIG. 1.
Figure 3:
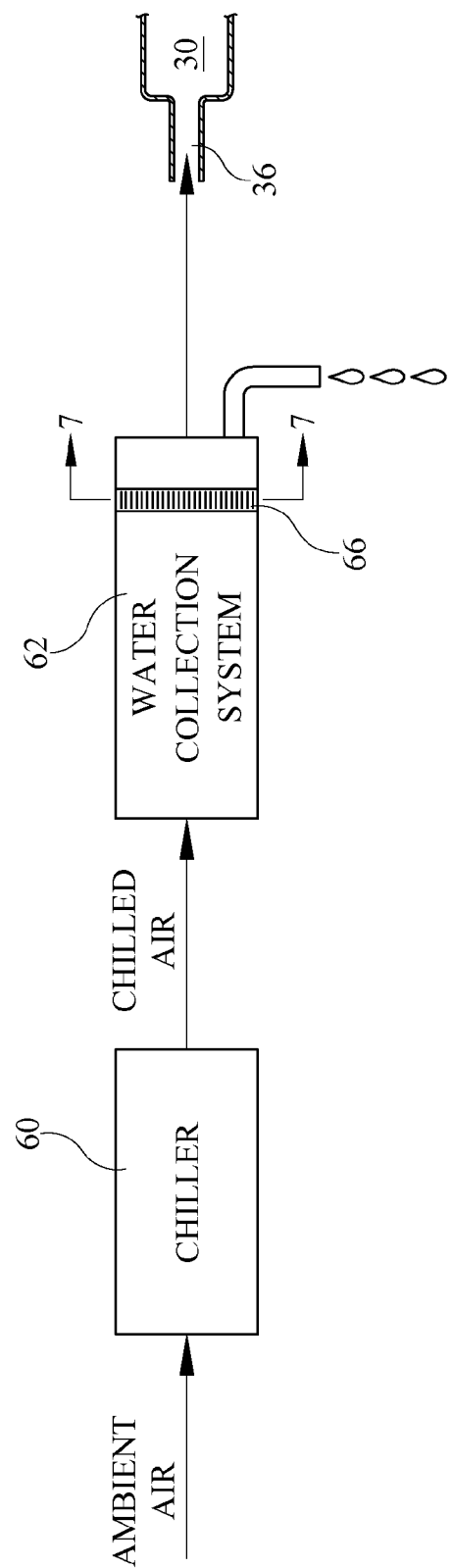
FIG. 3 is a schematic of a microclimate management system including a chiller and a water collection system as disclosed herein.
Figure 4:
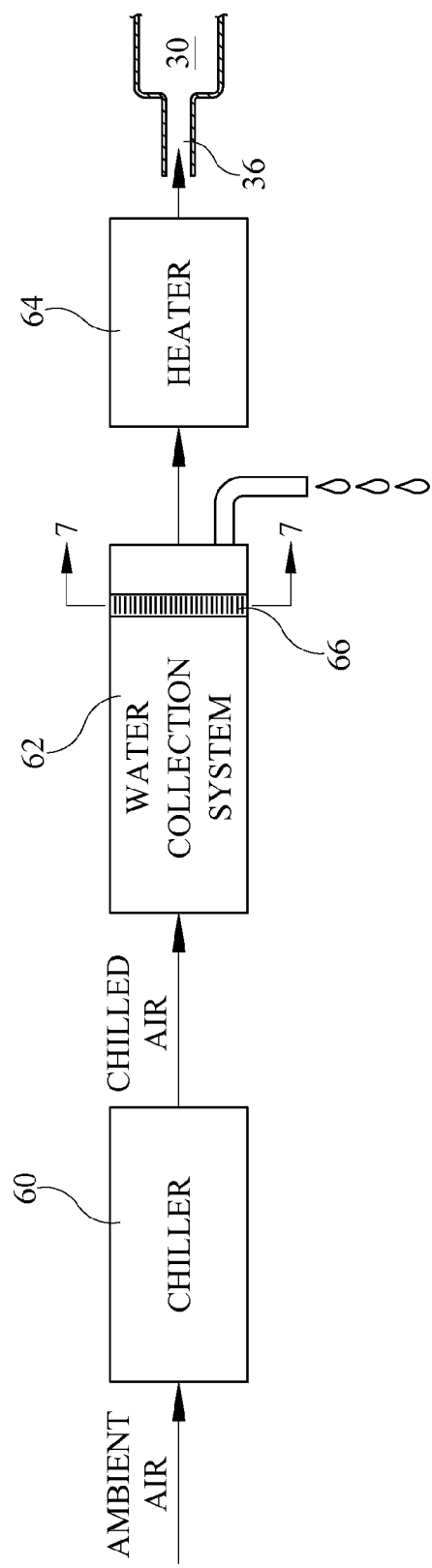
FIG. 4 is a schematic of a microclimate management system similar to that of FIG. 3 but also including a heater.

Referring to FIGS. 1-2, a bed 20 has a support surface 22 with microclimate management (MCM) capability. The MCM-capable support surface is depicted as a topper installed on top of a non-MCM-capable mattress, but could instead be the mattress itself. The support surface supports an occupant 24. The support surface comprises a material layer 26 bounding and at least partly defining an internal fluid flowpath 30. Portion 32 of the support surface is the portion upon which the occupant rests, and is vapor permeable. The support surface includes an air intake 36 and an air exhaust vent 38. During operation a stream 40 of air flows through the flowpath to serve as a sink for heat and water vapor. The bed also includes a user interface 42 for receiving user instructions concerning the operation of a microclimate management system (FIGS. 3, 4). The illustrated user interface includes a keypad 44 for receiving the user's instructions and a display panel 46 for conveying information to the user. The bed also includes a controller 50, responsive to the user's instructions, for controlling the microclimate management system. Referring to FIGS. 3-4, the microclimate management system includes a chiller 60, a water collection system 62 and, in one embodiment, a heater 64.

Before further describing the method and system for enhanced microclimate management, it will be useful to establish certain definitions and concepts.

Two principal mechanisms of heat transfer affect the microclimate. One mechanism, dry heat transfer, is proportional to temperature difference and is independent of the presence or absence of liquid phase perspiration at the occupant/surface interface. The potential of the support surface to effect dry heat transfer at a given temperature difference is referred to as its dry flux capacity, DFC. The dry heat transfer actually realized during operation of the system described herein is the actual dry flux, DF. Because the dry heat transfer is independent of whether or not liquid phase perspiration is present at the occupant/surface interface, the actual dry flux DF equals the dry flux capacity DFC:

$$DF=DFC=(1/R_{DRY})(T_{SKIN}-T_{STREAM}) \qquad (1)$$

where:

$R_{DRY}$ is a property of the MCM-capable surface 22, (particularly portion 32 of the support surface) in combination with the condition (e.g. temperature and flow rate) of the air stream 40 and the proximity of the airstream to the occupant's skin. Specifically, $R_{DRY}$ is a system constant that characterizes the resistance of the support surface and airstream to dry heat flow. The inverse, $1/R_{DRY}$, has units of power per unit area per temperature degree, for example watts/meter$^2$/° C. Low values of $R_{DRY}$ correspond to high heat transfer; high values of $R_{DRY}$ correspond to low heat transfer. In the examples presented below $R_{DRY}$ has a value of 0.300 (m$^{2\circ}$ C.)/watt.

$T_{SKIN}$ is the temperature of the occupant's skin at the occupant/surface interface. $T_{SKIN}$ has units of temperature such as degrees Centigrade (° C.); and $T_{STREAM}$ is the temperature of the air stream 40. For purposes of the present disclosure and the accompanying numerical example, and in many practical applications, $T_{STREAM}$ can be approximated as being equal to the ambient room air temperature, $T_{AMBIENT}$. Such an approximation neglects the effect of temperature changes imparted to the ambient air as it travels to and through the topper. These temperature changes may be due to a number of factors such as temperature changes associated with pressurizing the room ambient air to cause it to flow through the topper, heat transfer arising from heat rejection by nearby electronic components, and heat transferred into the airstream from the occupant. $T_{STREAM}$ has units of temperature such as degrees Centigrade (° C.).

Dry flux capacity DFC and dry flux DF have units of power per unit area, for example watts/meter$^2$.

The value of $R_{DRY}$ for a given system can be determined experimentally by way of a "dry plate test". A dry test plate, heated to a test temperature of 36° C. (a reasonable "standard" human skin temperature based on extensive measurements) is placed on a surface. A stream of air at a known temperature lower than 36° C. is caused to flow along the opposite side of the surface. Energy is supplied to the plate at a rate sufficient to maintain its temperature at 36° C. despite the cooling effect of the test airstream. These numerical values are used in equation (1) (36° is used as the value of $T_{SKIN}$; the temperature of the test air stream is used as the value of $T_{STREAM}$; the power per unit area of test plate supplied to keep the test plate at a constant temperature of 36° is used as the value of dry flux, DF). Equation (1) can then be solved for $R_{DRY}$.

The second mechanism of heat transfer, wet heat transfer, is proportional to the difference in the partial pressure of water vapor (perspiration) at the occupant's skin and the partial pressure of water vapor in the airstream 40. The potential of the support surface to effect wet heat transfer is its wet flux capacity, WFC. The wet heat transfer actually realized during operation of the system described herein is the actual wet flux, WF. The wet flux capacity WFC is realized as actual wet flux WF when perspiration is available for evaporation at the skin/surface interface. The rates of potential and actual wet heat transfer are referred to as wet flux capacity WFC and wet flux WF respectively, and can be expressed as:

$$WFC=(1/R_{WET})(P_{H2O,SKIN}-P_{H2O,STREAM}) \qquad (2A)$$

$$WF=(1/R_{WET})(P_{H2O,SKIN}-P_{H2O,STREAM}) \qquad (2B)$$

where:

$R_{WET}$ is a property of the MCM-capable support surface 22 (particularly portion 32 of the support surface) in combination with the condition (e.g. temperature and flow rate) of the air stream 40 and the proximity of the airstream to the occupant's skin. Specifically, $R_{WET}$ is a system constant that characterizes the resistance of the support surface and airstream to evaporative cooling. Its inverse, $1/R_{WET}$ has units of power per unit area per unit pressure, for example watts/meter$^2$/pascal. Low values of $R_{WET}$ correspond to high evaporative heat transfer; high values of $R_{WET}$ correspond to low evaporative heat transfer. In the examples presented below $R_{WET}$ has a value of 250 (m$^2$ Pa)/watt.

$P_{H2O,SKIN}$ is the partial pressure of water vapor (perspiration) at the occupant's skin (i.e. at the occupant/surface interface) $P_{H2O,SKIN}$ has units of pressure such as Pascals (Pa); and $P_{H2O,STREAM}$ is the partial pressure of water vapor in the airstream 40. If $T_{STREAM}$ is approximated as being equal to $T_{AMBIENT}$, $P_{H2O,STREAM}$ can be approximated as being equal to the partial pressure of water vapor at room air ambient temperature. $P_{H2O,STREAM}$ has units of pressure such as Pascals (Pa).

Although the right sides of equations 2A and 2B are identical in form, equation 2A applies without restriction because it describes the potential or capacity of the system. The applicability of equation 2B is restricted to those conditions when liquid perspiration is being deposited at the occupant/surface interface because it describes the actual wet heat transfer, which materializes only when liquid perspiration is being made available for evaporation.

Wet flux capacity WFC and wet flux WF have units of power per unit area, for example watts/meter$^2$.

The value of $R_{WET}$ for a given system can be determined experimentally by way of a "wet plate test". First, a dry plate test is conducted as described above. The test is then repeated with a supply of water directed to the plate to ensure that the entire test plate remains wet throughout the test. Energy is supplied to the plate at a rate sufficient to maintain its temperature at 36° C. despite the combined effect of dry heat transfer and evaporative cooling attributable to the test airstream. Appropriate numerical values from the test are then substituted into equation (2A or 2B). The value used for WF (or WFC) is the difference between the power supplied to the test plate during the wet phase of the test and the power supplied during the dry phase of the test. Because liquid moisture is present at the test plate/surface interface during the test, the value used for $P_{H2O,SKIN}$ is 5946 Pa, which is the partial pressure of water vapor at 36° C. and 100% relative humidity (i.e. the saturation pressure). $P_{H2O,STREAM}$ is determined by multiplying measured relative humidity of the ambient room air by the saturation pressure of water vapor at the prevailing room temperature. Equation (2) can then be solved for $R_{WET}$.

As is evident from the foregoing, $R_{DRY}$ and $R_{WET}$ are system specific constants, i.e. they are properties of the material used to make the surface, or at least the surface portion 32 of interest, of the condition of the airstream 40 passing through the support surface and of the proximity of the airstream to the occupant's skin. The factors $T_{STREAM}$, $T_{SKIN}$, $P_{H2O,STREAM}$ and $P_{H2O,SKIN}$ are environmental related factors because their values depend on the temperature and humidity of the room air and the conditions prevalent at the occupant's skin.

Total heat withdrawal capacity THWC is the sum of dry flux capacity DFC and wet flux capacity WFC. Actual total heat withdrawal THW is the sum of dry flux DF and wet flux WF:

$$THWC = DFC + WFC \tag{3A}$$

$$THW = DF + WF \tag{3B}$$

For the present application, it is useful to represent wet flux capacity and wet flux, which have units of energy per unit time per unit area, as an evaporative capacity EC and an evaporative rate ER, which have units of mass (of water) per unit time per unit area. At approximately 36° C. the heat of vaporization of water is about 2420 joules per gram. In other words it takes about 2420 joules (2420 watt-seconds or 0.672 watt-hours) of energy to evaporate one gram of water. Accordingly, one watt/m² of wet flux capacity corresponds to 1.489 gm/hour/m² of evaporative capacity, and one watt/m² of actual wet flux corresponds to 1.489 gm/hour/m² of actual evaporative rate:

$$EC = 1.489 \, WFC \tag{4A}$$

$$ER = 1.489 \, WF \tag{4B}$$

where:

EC and ER are evaporative capacity and evaporative rate expressed in grams per hour per square meter, 1.489 is the inverse of the heat of vaporization of water at 36° C. expressed in grams per joule, and WFC and WF are wet flux capacity and actual wet flux expressed in grams per watt-hour.

Using Equations (1), (2A) and (2B), equations (3A) and (3B) can be rewritten as:

$$THWC = (1/R_{DRY})(T_{SKIN} - T_{STREAM}) + (1/R_{WET})(P_{H2O,SKIN} - P_{H2O,STREAM}) \tag{5A}$$

$$THW = (1/R_{DRY})(T_{SKIN} - T_{STREAM}) + (1/R_{WET})(P_{H2O,SKIN} - P_{H2O,STREAM}) \tag{5B}$$

or alternatively as:

$$THWC = (1/R_{DRY})(T_{SKIN} - T_{STREAM}) + EC/1.489 \tag{6A}$$

$$THW = (1/R_{DRY})(T_{SKIN} - T_{STREAM}) + ER/1.489 \tag{6B}$$

where:

$$EC = 1.489 \, WFC = (1.489/R_{WET})(P_{H2O,SKIN} - P_{H2O,STREAM}) \tag{7A}$$

$$ER = 1.489 \, WF = (1.489/R_{WET})(P_{H2O,SKIN} - P_{H2O,STREAM}) \tag{7B}$$

subject to the condition that the equations representing system potential or capacity (equations 5A, 6A, 7A) apply irrespective of whether or not liquid perspiration is being deposited at the occupant/surface interface, and the equations representing actual performance (equations 5B, 6B, 7B) apply only when liquid perspiration is being deposited at the occupant/surface interface.

If the values of the system constants $R_{DRY}$ and $R_{WET}$ and of the environmental parameters $T_{SKIN}$, $T_{STREAM}$, $P_{H2O,SKIN}$, $P_{H2O,STREAM}$ are known, equations (5A), (6A) and (7A) can be used to determine the potential total heat withdrawal THWC and the evaporative capacity EC available to cool the bed occupant. Similarly, equations (5B), (6B) and (7B) can be used to determine the actual total heat withdrawal THW and evaporation rate applied to the bed occupant provided the condition for using those equations (the presence of perspiration available for evaporation at the occupant/surface interface) is met. $T_{SKIN}$ can be determined from actual skin temperature measurements or can be represented by a standard value, such as 36° C. $P_{H2O,SKIN}$ can be represented as the partial pressure of water vapor at $T_{SKIN}$ and at the relative humidity prevailing at the occupant/surface interface. When there is liquid phase perspiration available for evaporation at the occupant/surface interface the relative humidity will be 100%. If a standard value of 36° C. is used as the value of $T_{SKIN}$, at 100% relative humidity, $P_{H2O,SKIN}$ can be expressed as 5946 Pa.

Alternatively, if a desired evaporative rate $ER_{DESIRED}$ is specified, the parameters $R_{WET}$, $R_{DRY}$, $T_{SKIN}$, $P_{H2O,SKIN}$, room ambient air temperature $T_{AMBIENT}$ and room relative humidity $RH_{AMBIENT}$ can be used to calculate stream conditions $T_{STREAM,REQUIRED}$ and $P_{H2O,STREAM,REQUIRED}$ required to achieve the specified evaporative rate and the resulting total heat withdrawal. Equations 5, 6 and 7 are rewritten below as equations 5C, 6C and 7C to reflect that evaporative rate is the user specified parameter whereas $T_{STREAM}$, $P_{H2O,STREAM}$, and THW are dependent parameters. Equations 5C through 7C assume the presence of perspiration to be evaporated at the skin/support surface interface.

$$WF_{REQUIRED} = ER_{DESIRED}/1.489 = (1/R_{WET})(P_{H2O,SKIN} - P_{H2O,STREAM,REQUIRED}) \tag{7C}$$

$$THW = (1/R_{DRY})(T_{SKIN} - T_{STREAM,REQUIRED}) + (1/R_{WET})(P_{H2O,SKIN} - P_{H2O,STREAM,REQUIRED}) \tag{5C}$$

or alternatively:

$$THW = (1/R_{DRY})(T_{SKIN} - T_{STREAM,REQUIRED}) + ER_{DESIRED}/1.489 \tag{6C}$$

As another alternative, if a desired total heat withdrawal $THW_{DESIRED}$ is specified and exceeds the pre-existing total heat withdrawal, the desired total heat withdrawal might be obtainable by increasing dry flux alone, or may require a combination of increased wet flux and increased dry flux, although the apportionment of dry flux and wet flux cannot be independently specified for a given $THW_{DESIRED}$. Indeed, some specifications of total heat withdrawal may require more wet flux (evaporative cooling) than is desired. Equations 5, 6 and 7 are rewritten below as equations 5D, 6D and 7D to reflect that THW is the user specified parameter whereas stream conditions $T_{STREAM}$, $P_{H2O,STREAM}$ and EC are dependent parameters. Equations 5D through 7D assume the presence of perspiration to be evaporated at the skin/support surface interface.

$$THW_{DESIRED} = (1/R_{DRY})(T_{SKIN} - T_{STREAM,REQUIRED}) + (1/R_{WET})(P_{H2O,SKIN} - P_{H2O,STREAM,REQUIRED}) \tag{5D}$$

or alternatively:

$$THW_{DESIRED} = (1/R_{DRY})(T_{SKIN} - T_{STREAM,REQUIRED}) + ER_{REQUIRED}/1.489 \tag{6D}$$

where:

$$ER_{REQUIRED} = 1.489 WF_{REQUIRED} = (1.489/R_{WET})(P_{H2O,SKIN} - P_{H2O,STREAM,REQUIRED}) \quad (7D)$$

As noted above, the determination of required stream conditions by way of equations 5C-7C and 5D-7D can be simplified somewhat by using 36° C. as the value for $T_{SKIN}$, and using 5946 Pa, the vapor pressure of water at 36° C. and 1000 RH, as the value for $P_{H2O,SKIN}$.

Figure 6:
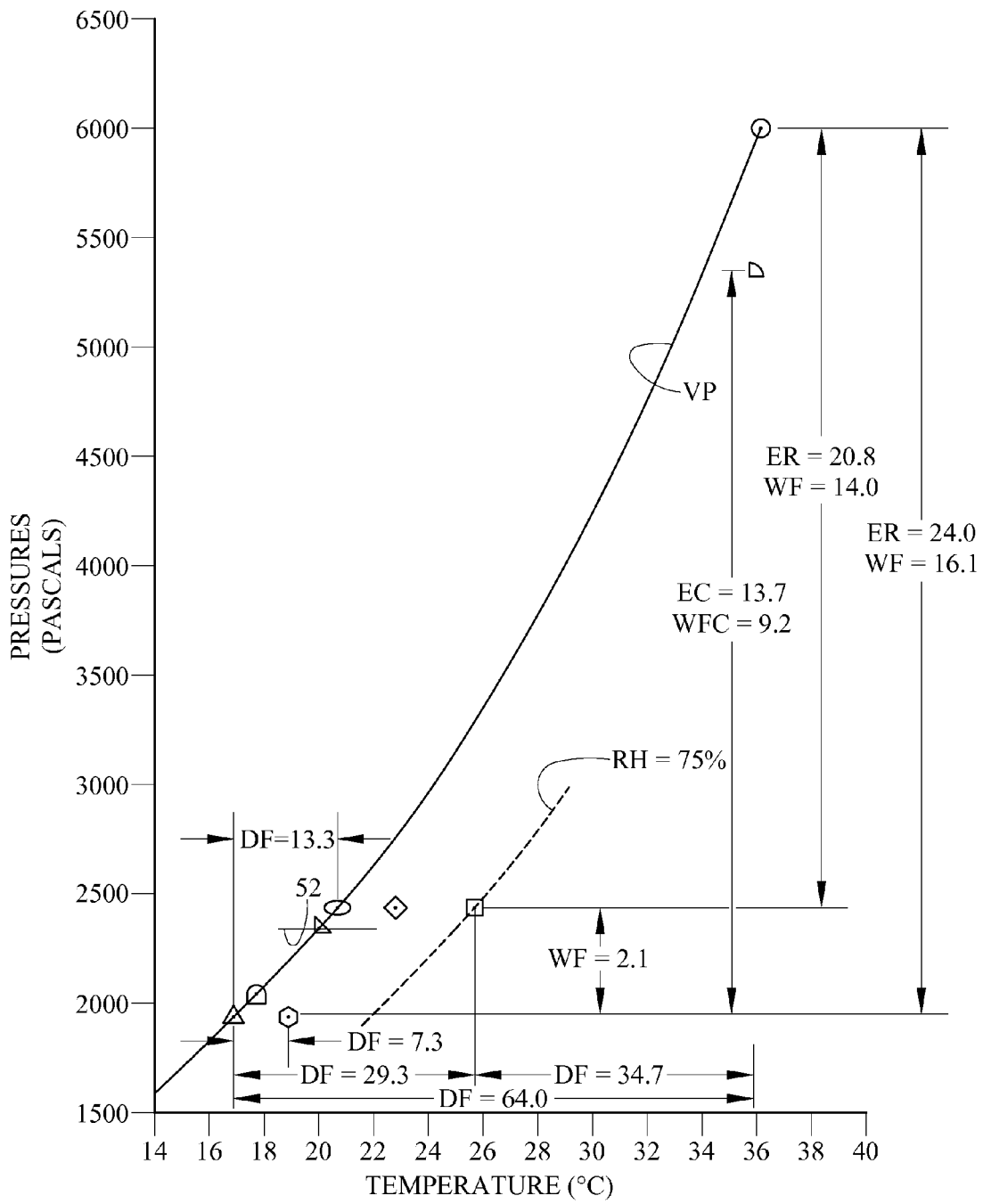
FIG. 6 is a graph showing vapor pressure of water as a function of temperature and including data symbols corresponding to numerical examples described herein.

Operation of the MCM-capable support surface and the microclimate management system of FIG. 3 can be understood by referring to the graph of FIG. 6 which shows pressure expressed in pascals (Pa) as a function of temperature expressed in ° C. Line VP represents the vapor pressure of water, and may also be referred to as the saturation line or as a line of 100% relative humidity, RH. The circular symbol represents a perspiring bed occupant whose skin temperature $T_{SKIN}$ is 36° C. Because of the perspiration at the occupant/support surface interface, the relative humidity at the interface is 100% which, at 36° C., corresponds to a vapor pressure of 5946 Pa.

The square symbol represents room ambient air, having a temperature of 25.6° C. and a relative humidity of 75%, corresponding to $P_{H2O,AMBIENT}$ of 2451 Pa. The room ambient air is unconditioned in the sense that no temperature or humidity conditioning has been applied to it above and beyond that applied by the facility HVAC equipment. If the airstream 40 flowing through the support surface flowpath 30 comprised this unconditioned ambient air, the occupant would experience, in accordance with equations (1) through (4) and with $R_{DRY}$=0.300 (m$^2$° C.)/watt and $R_{WET}$=250 (m$^2$ Pa)/watt:

ER=20.8 gm/hr/m$^2$, corresponding to a partial pressure difference of 3495 Pa;

WF=14.0 watt/m$^2$;

DF=34.7 watt/m$^2$, corresponding to a temperature difference of 10.4° C.; and

THW=48.7 watt/m$^2$

If it were desired to increase the evaporative cooling, a user such as a nurse or other caregiver would use keypad 44 to specify a desired evaporative rate ER of, for example, 24.0 gm/hr/m$^2$, which is greater than the 20.8 gm/hr/m$^2$ achievable with the unconditioned ambient air. In response to the user's instructions, controller 50 commands operation of chiller 60 to chill the ambient air to 16.8° C. (triangular symbol), which is lower than the 20.8° C. temperature required for the ambient air to be brought to a condition of 100% relative humidity (elliptical symbol). As seen on the graph, the chilling from 25.6° C. to 20.8° C. lowers the temperature of the air at a constant partial pressure of water vapor until relative humidity rises to 100%. This segment of the chilling process increases the dry flux capacity of the air (and also increases the actual dry flux) but, due to the absence of any change in partial pressure, does not increase its wet flux capacity or the actual wet flux. The cooling from 20.8° C. to 16.8° C. proceeds along saturation line VP and causes water vapor to condense, thereby demoisturizing the air (i.e. removing water molecules from the mixture of gas phase H$_2$O molecules and gaseous air). This segment of the chilling process has the intended effect of increasing wet flux capacity WFC and actual wet flux WF, and therefore evaporative capacity EC and evaporation rate ER (due to the reduction in partial pressure from 2451 Pa to 1916 Pa) and also further increases dry flux capacity and dry flux (due to the additional temperature reduction from 20.8° C. to 16.8° C.).

Figure 7:
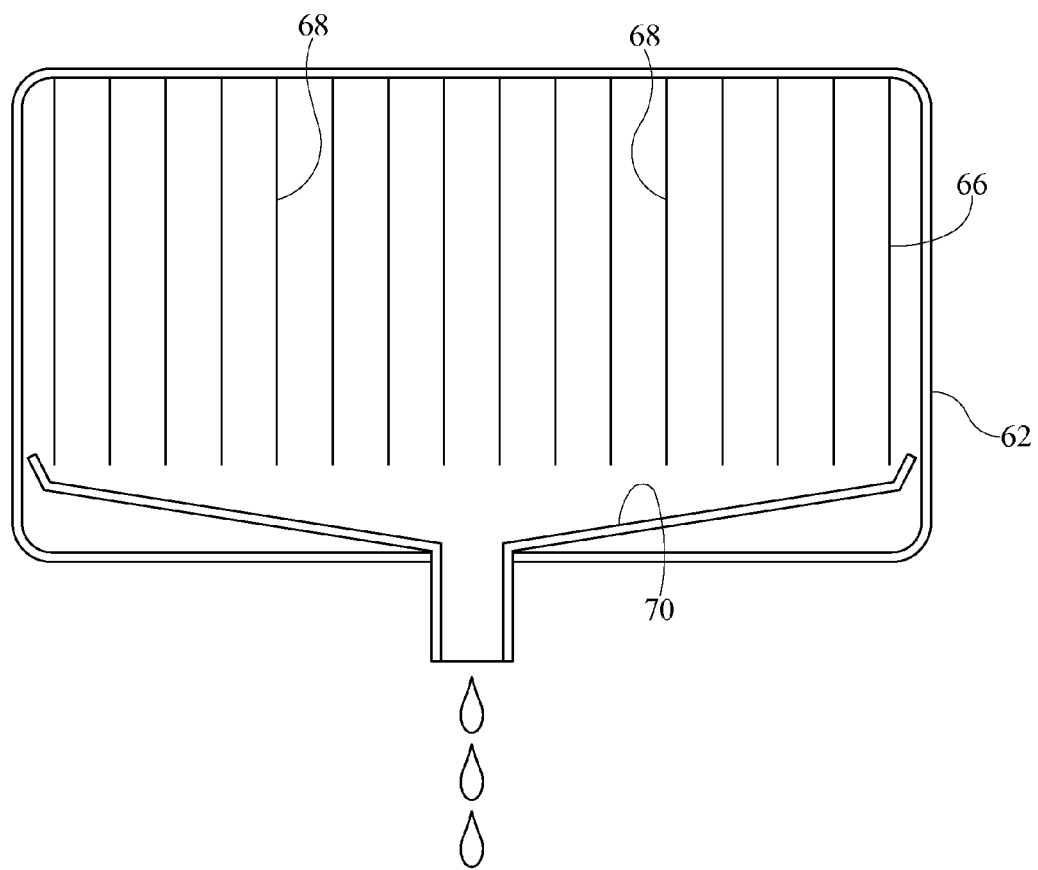
FIG. 7 is a view taken in direction 7-7 of FIG. 2 showing a nucleation device comprising an array of vertically oriented fibers.

The water removal system 62 drains or otherwise removes the liquid water. The illustrated water removal system includes a nucleation device 66 to promote and enhance the efficiency of the transition from the gaseous phase to the liquid phase. Referring to FIG. 7, one example nucleation device is a device having an array of vertically oriented fibers 68 projecting into airstream 40. The fibers converge into a funnel 70. Water droplets collect on the fibers. The weight of the water droplets causes them to migrate down the fibers where they drip into the funnel, which channels the water out of the system. The chilled, demoisturized air is then supplied to the support surface internal flowpath 30 where its enhanced dry flux capacity and wet flux capacity are manifested as actual heat transfer.

Table 1, below, compares the performance parameters of the microclimate management system using unconditioned ambient air (25.6° C. and 75% RH) and air chilled air as described above. Note that the 31.4 gm/hr/m$^2$ increase in total heat withdrawal comprises 2.1 gm/hr/m$^2$ of wet flux and 29.3 gm/hr/m$^2$ of dry flux. Of the 29.3 gm/hr/m$^2$ of dry flux, 13.3 gm/hr/m$^2$ is dry flux resulting from the cooling required to achieve the 2.1 gm/hr/m$^2$ of wet flux.

TABLE 1

| Parameter | Ambient Air | Chilled to 16.8° C. | Change |
|---|---|---|---|
| Temperature (° C.) | 25.6 | 16.8 | −8.8 |
| ER (gm/hr/m$^2$) | 20.8 | 24.0 | 3.2 |
| WF (watt/m$^2$) | 14.0 | 16.1 | 2.1 |
| $P_{H2O}$ (Pa) | 2451 | 1916 | −535 |
| DF (watt/m$^2$) | 34.7 | 64.0 | 29.3 |
| THW (watt/m$^2$) | 48.7 | 80.1 | 31.4 |

The above described method and system may, as a consequence of increasing the evaporative rate, result in more total heat withdrawal than is desired, a condition referred to herein as "overchilling". For example, the evaporative benefit of increasing the evaporative rate from 20.8 to 24.0 gm/hr/m$^2$ may be desired, but at least some of the total heat withdrawal may not be. Such a condition can be mitigated by using a heater 64 to heat the chilled, demoisturized air prior to the step of supplying it to flowpath 30. As a practical matter, the heater would be operated only if it were determined that the temperature of the chilled air was, or would be, unsatisfactorily low. Referring again to FIG. 6, the heating causes the temperature of the chilled, demoisturized air to increase from 16.8° C. to a higher value, for example 19.0° C. (hexagonal symbol). The heating step has no effect on the partial pressure of the water vapor in airstream 40, and hence no effect on the evaporative rate. However the temperature increase reduces the dry flux (in comparison to the dry flux at 16.8° C.). Table 2 summarizes the change in performance parameters of the microclimate management system using air chilled to 16.8° compared to air reheated to 19.0° C. Table 3 presents a similar comparison relative to the use of unconditioned ambient air at 25.6° C. and 75% RH.

TABLE 2

| Parameter | Chilled to 16.8° C. | reheated to 19.0° C. | Change |
|---|---|---|---|
| Temperature (° C.) | 16.8 | 19.0 | 2.2 |
| ER (gm/hr/m$^2$) | 24.0 | 24.0 | 0 |
| WF (watt/m$^2$) | 16.1 | 16.1 | 0 |
| $P_{H2O}$ (Pa) | 1916 | 1916 | 0 |
| DF (watt/m$^2$) | 64.0 | 56.7 | −7.3 |
| THW (watt/m$^2$) | 80.1 | 72.8 | −7.3 |

TABLE 3

| Parameter | Ambient Air | Chilled to 16.8° C. and reheated to 19.0° C. | Change |
| --- | --- | --- | --- |
| Temperature (° C.) | 25.6 | 19.0 | −6.6 |
| ER (gm/hr/m$^2$) | 20.8 | 24.0 | 3.2 |
| WF (watt/m$^2$) | 14.0 | 16.1 | 2.1 |
| P$_{H2O}$ (Pa) | 2451 | 1916 | −535 |
| DF (watt/m$^2$) | 34.7 | 56.7 | 22.0 |
| THW (watt/m$^2$) | 48.7 | 72.8 | 24.1 |

FIG. 6 also shows one example in which no liquid phase perspiration is being deposited at the occupant/surface interface. The example assumes 90% relative humidity and a temperature of 36° C. at the interface (quarter circle symbol). Accordingly, P$_{H2O,SKIN}$ is about 5351 Pa. A calculation of wet flux capacity WFC would show a potential for 9.2 watts/m$^2$ of heat transfer. The corresponding calculation of evaporative capacity would show a potential to remove about 13.7 gm/hour/m$^2$ of moisture (perspiration) from the occupant/surface interface. However these values of heat transfer and evaporation can be realized only if dry heat transfer first reduces the temperature to about 34.1° C. (the temperature corresponding to 100% relative humidity at 5351 Pa).

Figure 5A:
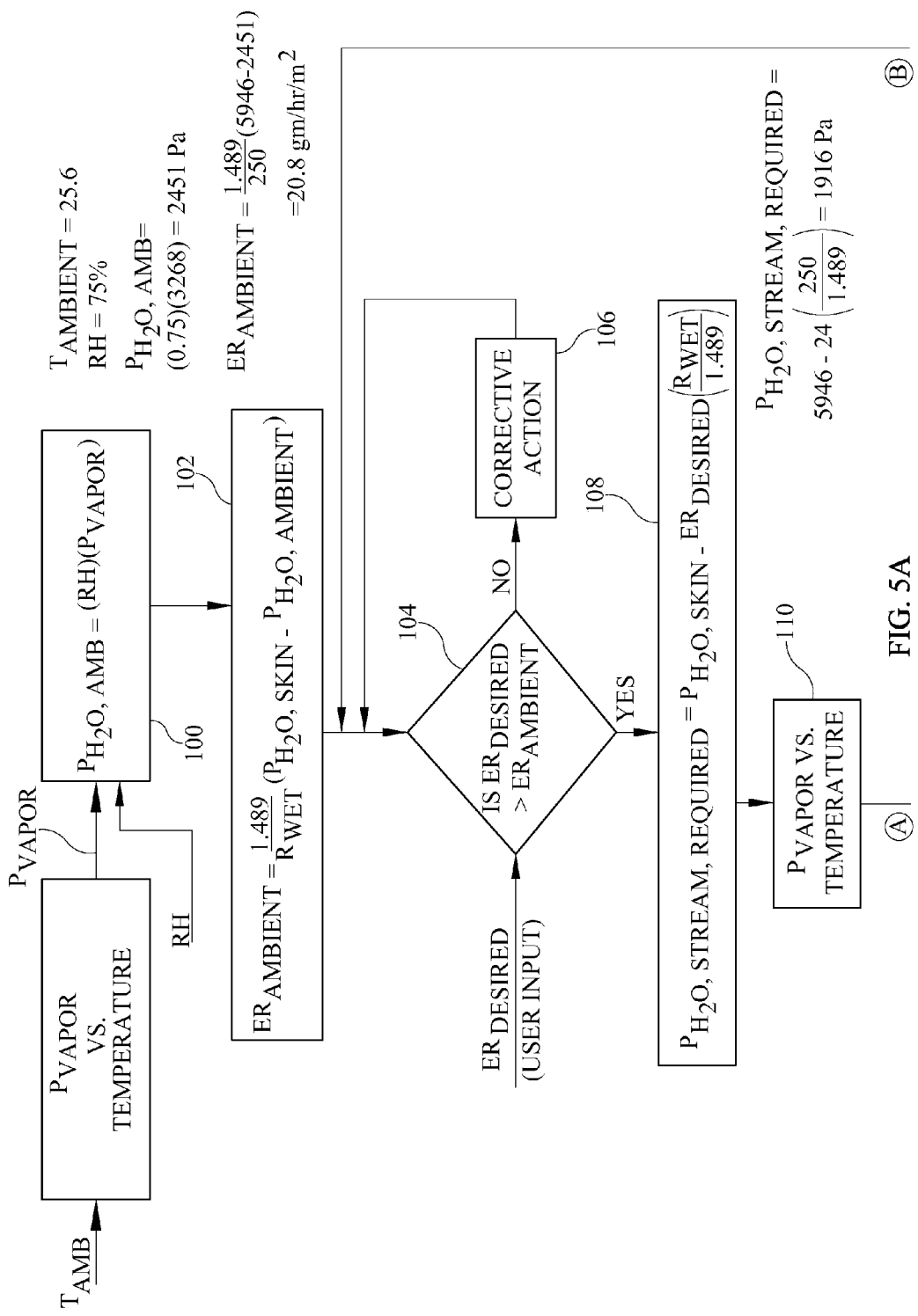
FIG. 5 is a block diagram of an algorithm for controlling evaporative capacity of a support surface.
Figure 5B:
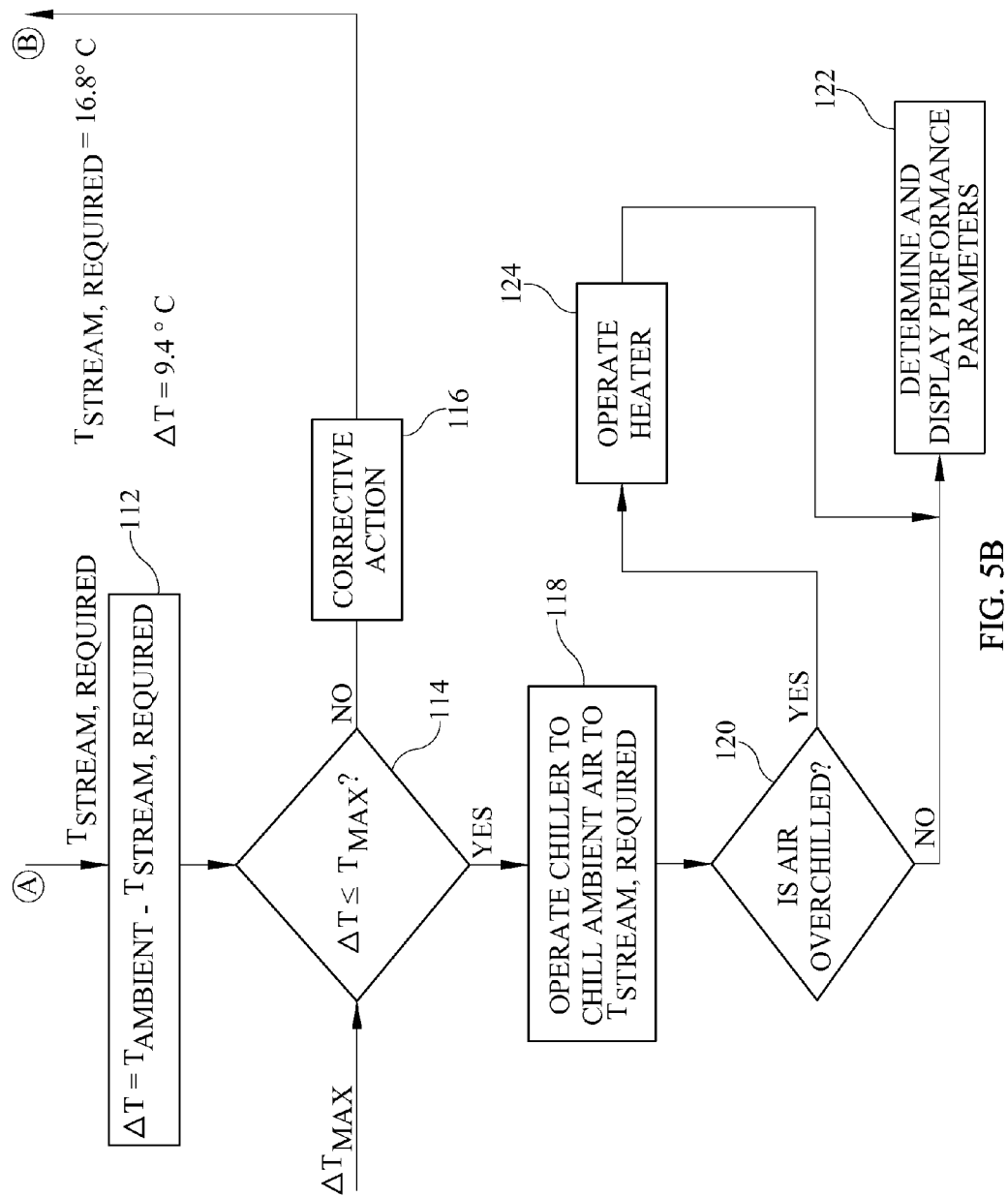

FIG. 5 is a block diagram of an algorithm for enhancing evaporative capacity of an MCM-capable support surface beyond that which could be achieved with unconditioned ambient air. The numerical values to the right of the diagram blocks are from the above examples, using 36° C. as the value for T$_{SKIN}$, and 5946 Pa, the vapor pressure of water at 36° C. and 100% RH, as the value for P$_{H2O,SKIN}$. At block 100 the algorithm calculates P$_{H2O,AMBIENT}$, the partial pressure of water vapor at the prevailing ambient conditions, as a function of relative humidity and the vapor pressure of water, P$_{VAPOR}$, which is a function of ambient temperature, T$_{AMB}$:

$$P_{H2O,AMBIENT} = (RH)(P_{VAPOR}) \quad (8)$$

P$_{VAPOR}$ may be determined in any convenient way, for example by using a lookup table consistent with saturation line VP of FIG. 6 or by an equation, such as third order equation (9), which gives vapor pressure in pascals as a function of temperature in ° C. Equation (9) models the saturation line satisfactorily between about 10° C. and 40° C.:

$$P_{VAPOR} = 0.0776(T_{AMB}^3) - 0.757(T_{AMB}^2) + 80.364(T_{AMB}) + 413.15 \quad (9)$$

Block 102 uses equations (2) and (4) to calculate ER$_{AMBIENT}$, the evaporative rate achievable with ambient air, assuming the presence of perspiration to be evaporated at the skin/support surface interface.

Block 104 assess whether or not a desired value of evaporative rate input by a user by way of keypad 44 exceeds the evaporative rate achievable with the unconditioned ambient air. If not the controller takes a "corrective action" at block 106 such as commanding display panel 46 to display one or more messages such as a message to prompt the user for an alternate desired value, a message offering guidance as to what evaporative rate values are acceptable, or a message asking the user to confirm that the evaporative rate achievable with ambient air is satisfactory. After the user provides an acceptable, desired evaporative rate, for example 24 gm/hr/m$^2$, the algorithm proceeds to block 108.

At block 108 the algorithm uses equation (7B) to calculate P$_{H2O,STREAM,REQUIRED}$, the partial pressure of water vapor required to achieve the desired evaporative rate.

At block 110 the algorithm again uses a relationship between vapor pressure and T$_{STREAM,REQUIRED}$, temperature to determine the temperature required to achieve the P$_{H2O,STREAM,REQUIRED}$ determined at block 108.

At blocks 112 and 114 the algorithm determines the difference ΔT between ambient temperature and the required temperature determined at block 110, and assesses whether or not the ΔT is within the known capability ΔT$_{MAX}$ of the chiller. If not, the controller takes a "corrective action" 116 such as commanding display panel 46 to display one or more messages such as a message to prompt the user for an alternate desired value of evaporative rate, or a message offering guidance as to what evaporative rate values are achievable. After the user provides an acceptable desired evaporative rate, the algorithm repeats the appropriate steps starting at block 104, and proceeds to block 118.

At block 118, the controller causes chiller 60 to operate to chill the ambient air to the required temperature, T$_{STREAM,REQUIRED}$, determined at block 110.

At block 120 the controller determines if chilling the ambient air to the required temperature determined at block 110 would result in an overchill condition. The test for overchill can take various forms, for example a pre-emptive or corrective command from a user, or a predefined limit for a particular occupant, a particular class of occupants or a limit established by a facility protocol. If the overchill test is not satisfied, the algorithm proceeds to block 122. If the test is satisfied, the algorithm proceeds to block 124 where the controller causes heater 64 to operate to heat the chilled, demoisturized air. The algorithm then proceeds to block 122.

At block 122, the algorithm determines one or more microclimate performance parameters and causes the parameters to be displayed on display panel 46. Table 4 lists examples of parameters of possible interest along with their numerical values from the above example.

TABLE 4

| Microclimate Performance Parameter | Example Value (Chill to 16.8° C. without reheating) | Example Value (Chill to 16.8° C.; reheat to 19.0° C.) |
| --- | --- | --- |
| Difference in evaporative rate attributable to the chilled, demoisturized air and the evaporative rate achievable with the unconditioned ambient air. | 3.2 | 3.2 |
| Ratio of the evaporative rate attributable to the chilled, demoisturized air and the evaporative rate achievable with the unconditioned ambient air; | 1.2 | 1.2 |

TABLE 4-continued

| Microclimate Performance Parameter | Example Value (Chill to 16.8° C. without reheating) | Example Value (Chill to 16.8° C.; reheat to 19.0° C.) |
|---|---|---|
| Difference in wet flux attributable to the chilled, demoisturized air and the wet flux achievable with the unconditioned ambient air | 2.1 | 2.1 |
| Ratio of the wet flux attributable to the chilled, demoisturized air and the wet flux achievable with the unconditioned ambient air | 1.2 | 1.2 |
| Difference in dry flux attributable to the chilled, demoisturized air and the dry flux achievable with the unconditioned ambient air | 29.3 | 22.0 |
| Ratio of the dry flux attributable to the chilled, demoisturized air and the dry flux achievable with the unconditioned ambient air; | 1.8 | 1.6 |
| Difference in total heat withdrawal attributable to the chilled, demoisturized air and the total heat withdrawal achievable with the unconditioned ambient air; | 31.4 | 24.1 |
| Ratio of the total heat withdrawal attributable to the chilled, demoisturized air and the total heat withdrawal achievable with the unconditioned ambient air. | 1.6 | 1.5 |

Referring again to FIG. 6, the principles disclosed herein can be used to allow the user to manage the performance of an MCM-capable support by specifying a target total heat withdrawal, rather than by specifying an evaporative rate. If dry flux alone is sufficient to achieve the target total heat withdrawal, the chiller is operated to chill the ambient air (square symbol) to a temperature low enough to achieve the desired target heat withdrawal (e.g. the diamond symbol). This temperature is, by definition, higher than the temperature corresponding to 100% relative humidity.

If dry flux alone is not sufficient to achieve the target total heat withdrawal, the chiller is operated to cool the air to a temperature at least as low as that required to achieve 100% relative humidity (20.8° C.) and also low enough to achieve the target total heat withdrawal (e.g. the domed symbol). Because achieving the target total heat withdrawal involves a wet flux component in addition to the dry flux component, the heat withdrawal will also cause airstream 40 to exert a drying influence on the bed occupant. If this results in excessive dryness, it may be desirable or necessary to sacrifice some of the wet flux. On the graph, an evaporative cooling limit is represented by limit 52, which is proportional to a predefined wet flux limit. Observance of the limit restricts operation of the chiller to achieving the total heat withdrawal at the wedge symbol. Table 5 shows example performance parameters of the system using ambient air (column 1), air chilled to achieve a total heat withdrawal of 58 watt/m$^2$ (column 2), air cooled to achieve a total heat withdrawal of 77 watt/m$^2$ (column 3) and air cooled to limit line 52 to achieve a total heat withdrawal of 67 watt/m$^2$ (column 4).

TABLE 5

| Parameter | 1 Using Ambient Air | 2 Chilled to Achieve THW = 58.0 | 3 Chilled to Achieve THW = 77.0 | 4 Observing 67.0 watt/m$^2$ THW (lower limit) |
|---|---|---|---|---|
| Temperature (° C.) | 25.6 | 22.8 | 17.6 | 20.2 |
| ER (gm/hr/m$^2$) | 20.8 | 20.8 | 23.4 | 21.3 |
| WF (watt/m$^2$) | 14.0 | 14.0 | 15.7 | 14.3 |
| $P_{H2O}$ (Pa) | 2451 | 2451 | 2016 | 2367 |
| DF (watt/m$^2$) | 34.7 | 44.0 | 61.3 | 52.7 |
| THW (watt/m$^2$) | 48.7 | 58.0 | 77.0 | 67.0 |

In view of the foregoing, certain additional aspects of the method and system can be appreciated. For example the sequence in which certain steps of the algorithms may be changed. For example, a test for overchilling may be carried out after the chiller has chilled the ambient air, or it may be carried out prior to chilling, provided there is some foreknowledge of how much chilling qualifies as overchilling.

Figure 8A:
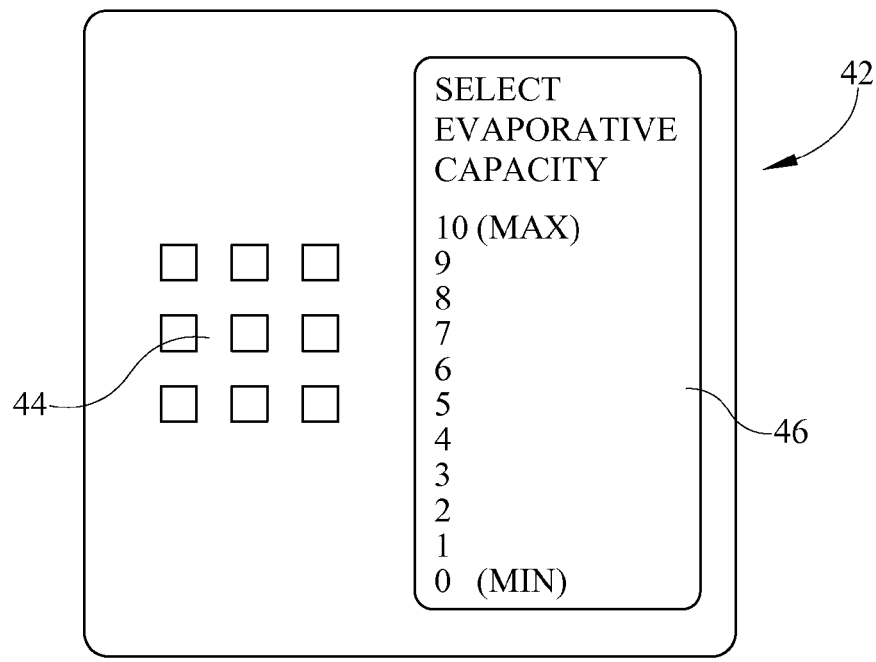
FIGS. 8A and 8B are views of a user interface showing two possible ways for permitting a caregiver to specify a desired performance of the microclimate management system.
Figure 8B:
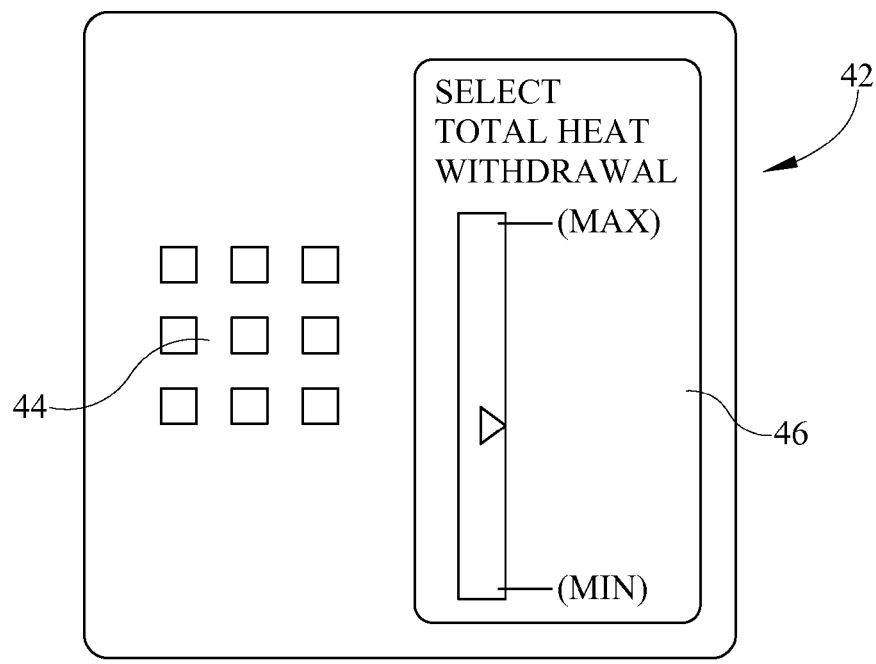

The foregoing numerical examples suggest that a caregiver would specify a desired numerical value of evaporative rate (mass per unit time per unit area) or total heat withdrawal (power per unit area). Alternatively, as seen in FIG. 8, the user interface could present the user with a discrete scale extending from "0" to "10", a continuous scale extending from minimum evaporative rate or total heat withdrawal to a maximum evaporative rate or total heat withdrawal, or some other less technical means for specifying desired performance of the system.

Although this disclosure refers to specific embodiments, it will be understood by those skilled in the art that various changes in form and detail may be made without departing from the subject matter set forth in the accompanying claims.

I claim:

1. A method for controlling performance of an MCM capable support surface having a flowpath for guiding a stream of air along at least a portion of the surface, comprising:
   measuring the temperature of the skin of a patient positioned on the surface;
   receiving an input indicative of a desired evaporative rate greater than an evaporative rate achievable with unconditioned ambient air;
   chilling unconditioned ambient air to a temperature at least as low as that required to achieve 100% relative humidity, thereby demoisturizing the air;
   receiving an input indicative of a desired total heat withdrawal rate less than a total heat withdrawal rate achievable with the chilled air;
   adding heat to the demoisturized air without adding moisture to the demoisturized air, the amount of heat added being based on the temperature of the skin of the patient; and
   supplying the heated and demoisturized air to the flowpath to achieve the desired evaporation rate and the desired total heat withdrawal rate.

2. The method of claim 1 comprising determining a microclimate performance parameter and determining the heat to be added to the demoisturized air based on the microclimate performance parameter and on the temperature of the skin of the patient.

3. The method of claim 2 wherein the microclimate performance parameter is:
   the ratio of the total heat withdrawal attributable to the chilled, demoisturized air and the total heat withdrawal achievable with the unconditioned ambient air.

4. The method of claim 1 comprising determining if the total heat withdrawal rate of the chilled, demoisturized air is unsatisfactorily high; and
   carrying out the heating step only if the total heat withdrawal rate of the chilled air is determined to be unsatisfactorily high.

5. The method of claim 2 wherein the microclimate performance parameter is the difference in total heat withdrawal attributable to the chilled, demoisturized air and the total heat withdrawal achievable with the unconditioned ambient air.

6. The method of claim 2 wherein the microclimate performance parameter is the ratio of the dry flux attributable to the chilled, demoisturized air and the dry flux achievable with the unconditioned ambient air.

7. The method of claim 2 wherein the microclimate performance parameter is the ratio of the wet flux attributable to the chilled, demoisturized air and the wet flux achievable with the unconditioned ambient air.

8. The method of claim 2 wherein the microclimate performance parameter is the difference in wet flux attributable to the chilled, demoisturized air and the wet flux achievable with the unconditioned ambient air.

9. The method of claim 2 wherein the microclimate performance parameter is the ratio of the evaporative rate attributable to the chilled, demoisturized air and the evaporative rate achievable with the unconditioned ambient air.

10. The method of claim 2 wherein the microclimate performance parameter the difference in evaporative rate attributable to the chilled, demoisturized air and the evaporative rate achievable with the unconditioned ambient air.

11. A method for controlling performance of an MCM capable support surface having a flowpath for guiding a stream of air along at least a portion of the surface, comprising:
    measuring the temperature of the skin of a patient positioned on the surface;
    chilling the unconditioned ambient air to a temperature at least as low as that required to achieve 100% relative humidity, thereby demoisturizing the air;
    receiving an input indicative of a desired total heat withdrawal rate less than a total heat withdrawal rate achievable with the chilled air;
    adding heat to the demoisturized air without adding moisture to the demoisturized air, the amount of heat added being based on the temperature of the skin of the patient; and
    supplying the heated and demoisturized air to the flowpath to achieve the desired total heat withdrawal rate.

12. The method of claim 11 comprising determining a microclimate performance parameter and determining the heat to be added to the demoisturized air based on the microclimate performance parameter and on the temperature of the skin of the patient.

13. The method of claim 12 wherein the microclimate performance parameter the ratio of the total heat withdrawal attributable to the chilled, demoisturized air and the total heat withdrawal achievable with the unconditioned ambient air.

14. The method of claim 12 wherein the microclimate performance parameter is the difference in total heat withdrawal attributable to the chilled, demoisturized air and the total heat withdrawal achievable with the unconditioned ambient air.

15. The method of claim 12 wherein the microclimate performance parameter is the ratio of the dry flux attributable to the chilled, demoisturized air and the dry flux achievable with the unconditioned ambient air.

16. The method of claim 12 wherein the microclimate performance parameter is the ratio of the wet flux attributable to the chilled, demoisturized air and the wet flux achievable with the unconditioned ambient air.

17. The method of claim 12 wherein the microclimate performance parameter is the difference in wet flux attributable to the chilled, demoisturized air and the wet flux achievable with the unconditioned ambient air.

18. The method of claim 12 wherein the microclimate performance parameter is the ratio of the evaporative rate attributable to the chilled, demoisturized air and the evaporative rate achievable with the unconditioned ambient air.

19. The method of claim 12 wherein the microclimate performance parameter the difference in evaporative rate attributable to the chilled, demoisturized air and the evaporative rate achievable with the unconditioned ambient air.

20. The method of claim 11 comprising determining if the total heat withdrawal rate of the chilled, demoisturized air is unsatisfactorily high; and carrying out the heating step only if the total heat withdrawal rate of the chilled air is determined to be unsatisfactorily high.

* * * * *